United States Patent [19]

Phillips et al.

[11] Patent Number: 5,324,298
[45] Date of Patent: Jun. 28, 1994

[54] ENDOSCOPIC KNOT PUSHING INSTRUMENT

[75] Inventors: Edward H. Phillips, 712 N. Roxbury, Beverly Hills, Calif. 90210; Steve Raiken, Culver City, Calif.

[73] Assignee: Edward H. Phillips, Beverly Hills, Calif.

[21] Appl. No.: 970,702

[22] Filed: Nov. 3, 1992

[51] Int. Cl.$^5$ .............................................. A61B 17/00
[52] U.S. Cl. ......................................... 606/148; 289/17
[58] Field of Search ................ 606/139, 148, 144; 289/17

[56] References Cited

U.S. PATENT DOCUMENTS

| | | | |
|---|---|---|---|
| 3,131,957 | 5/1964 | Musto | 289/17 |
| 3,625,556 | 12/1971 | Stromberg | 289/17 |
| 5,084,058 | 1/1992 | Li | 606/148 |
| 5,176,691 | 1/1993 | Pierce | 606/144 |
| 5,234,444 | 8/1993 | Christoudias | 606/148 |

Primary Examiner—Tamara L. Graysay
Attorney, Agent, or Firm—Frederick Gotha

[57] ABSTRACT

An instrument is set forth for pushing a knot formed extracorporeally through a trocar and into the operative region during endoscopic surgery. An elongated member having an axially extending groove at its distal end is dimensioned to permit the axial advance of a strand of suture material through the groove. A locking sleeve is carried by the elongated member at its distal end and adapted for rotation relative to the elongated member. The locking sleeve has an axially extending slit which in one position may be aligned with the groove for insertion of the suture strand. By rotating the sleeve to a second position, the suture strand is captively retained within the groove so as to permit axial advance of the suture strand as the knot is pushed through the trocar.

14 Claims, 4 Drawing Sheets

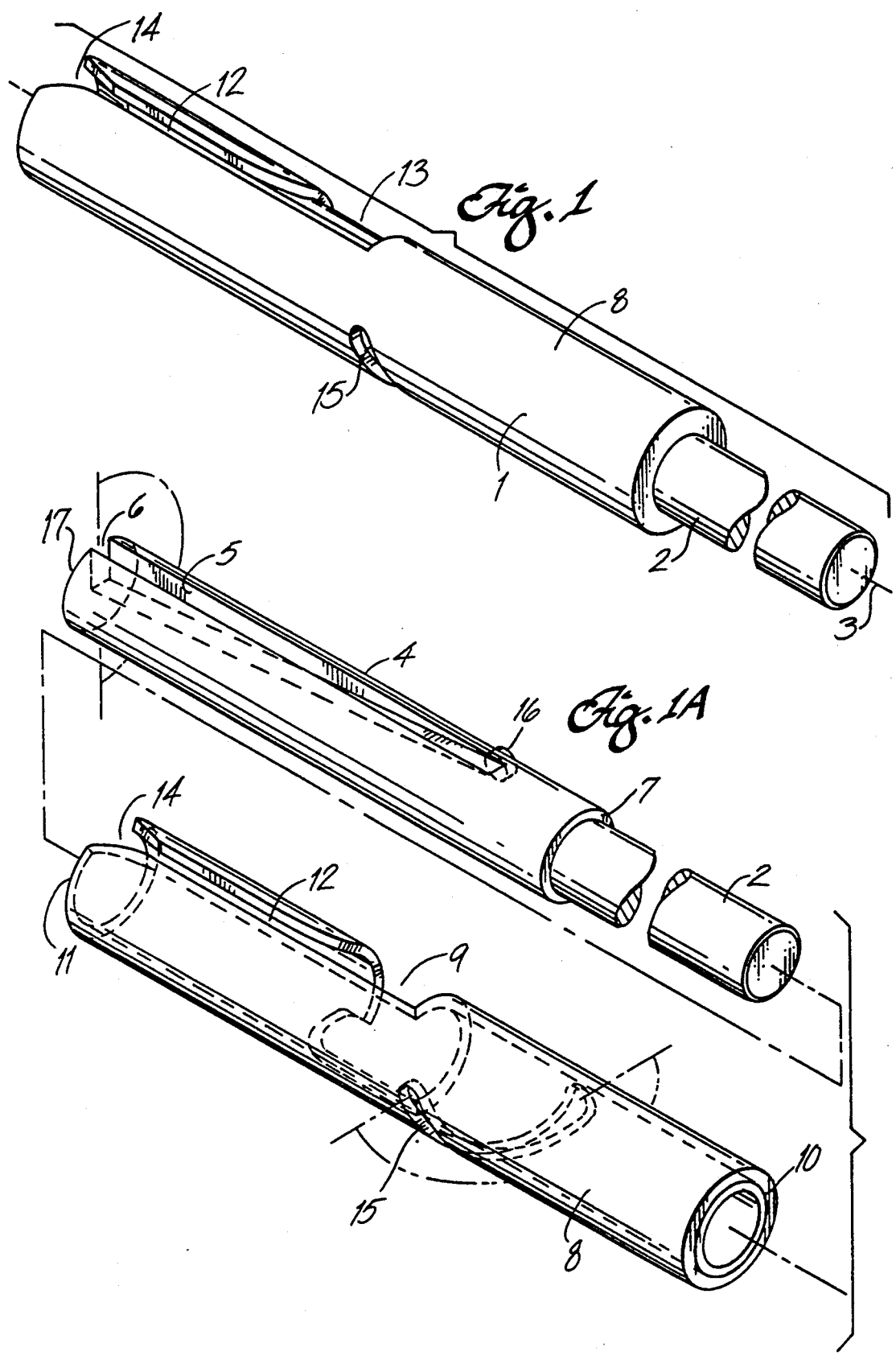

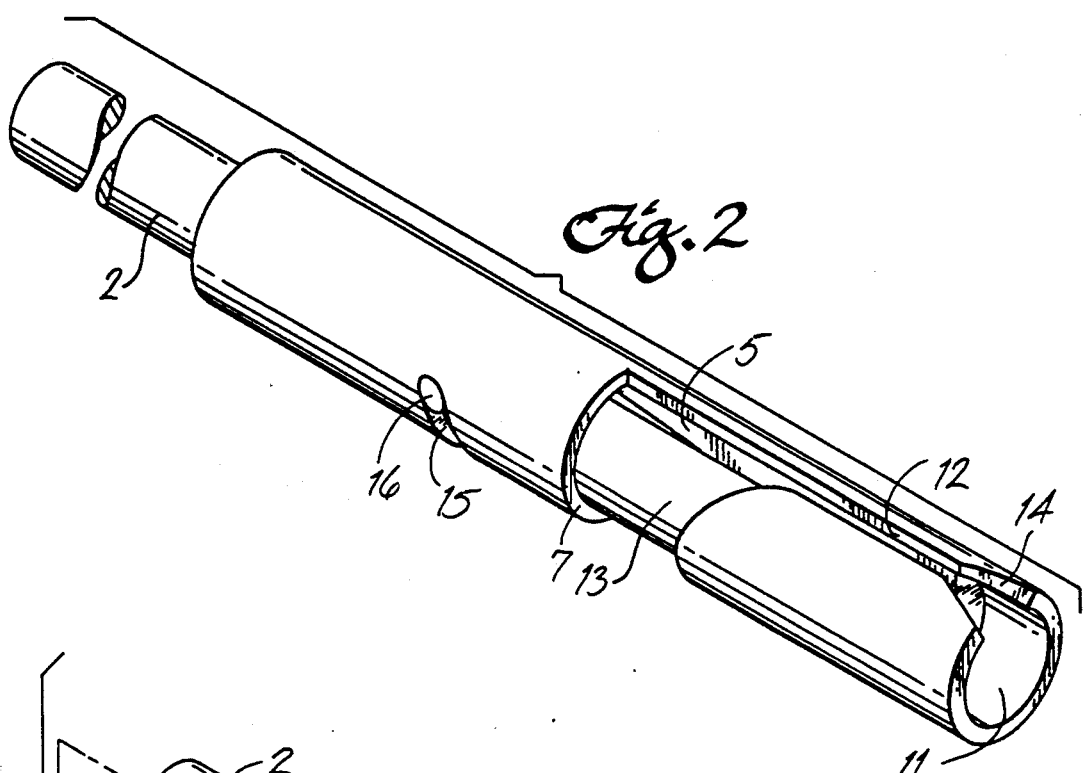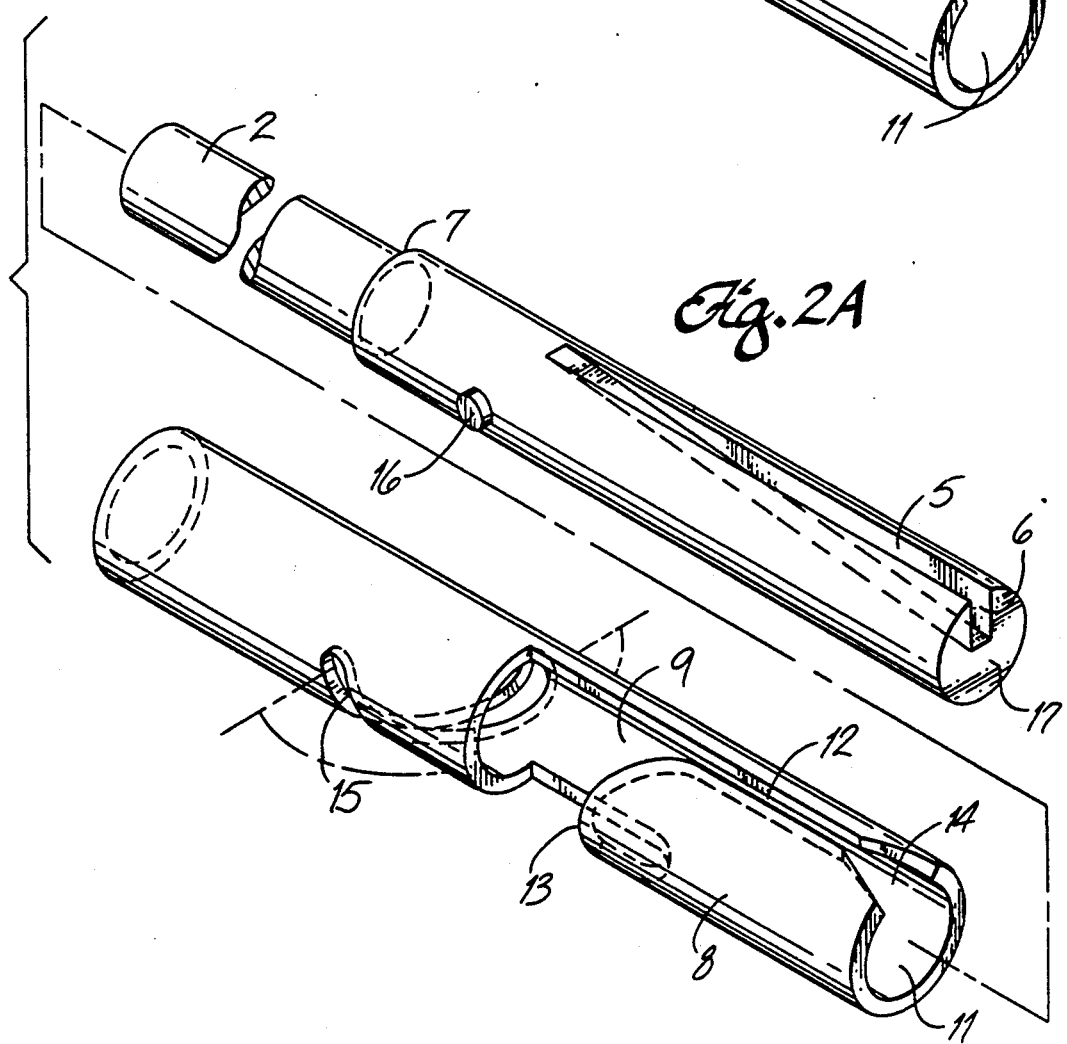

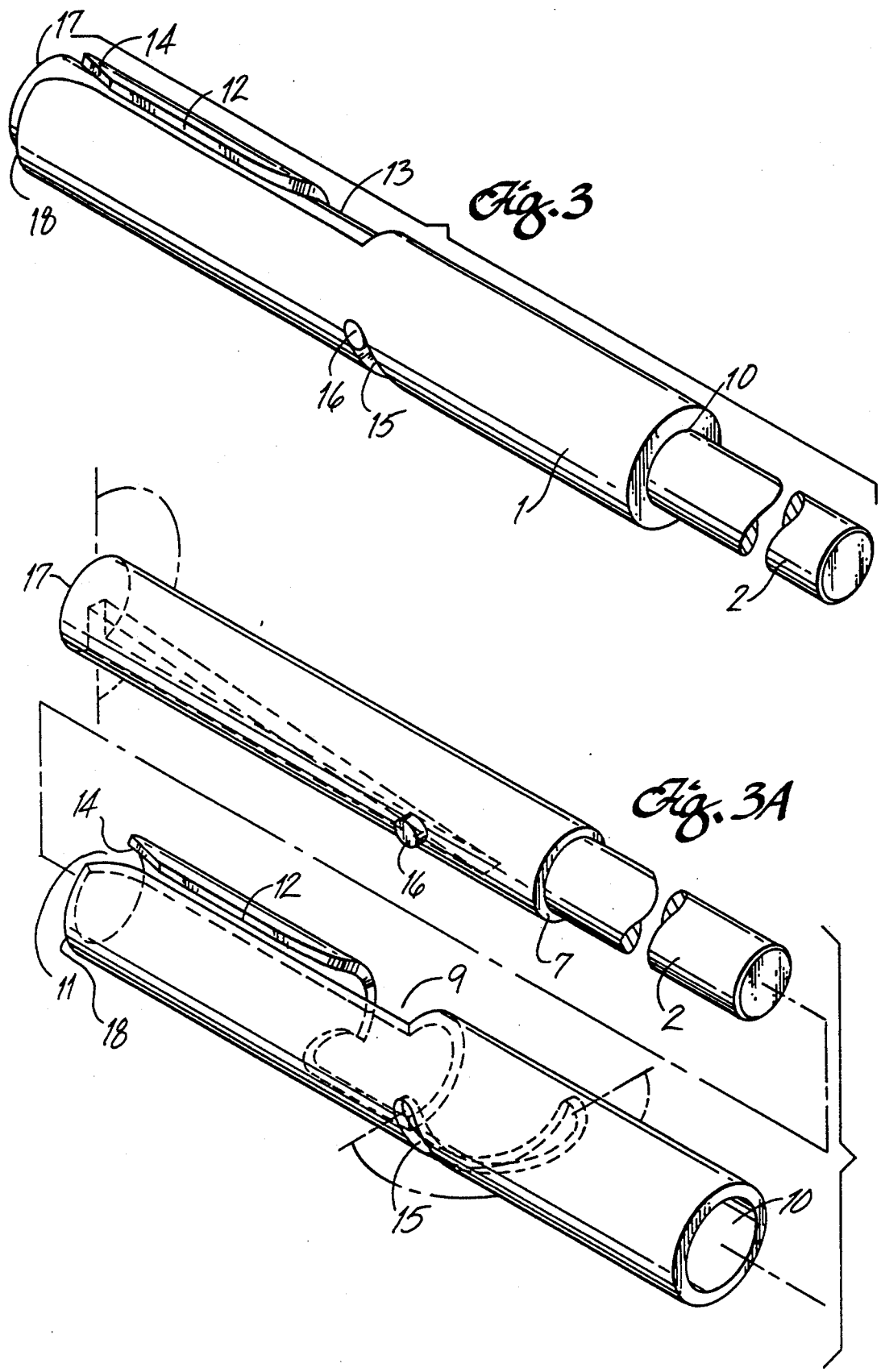

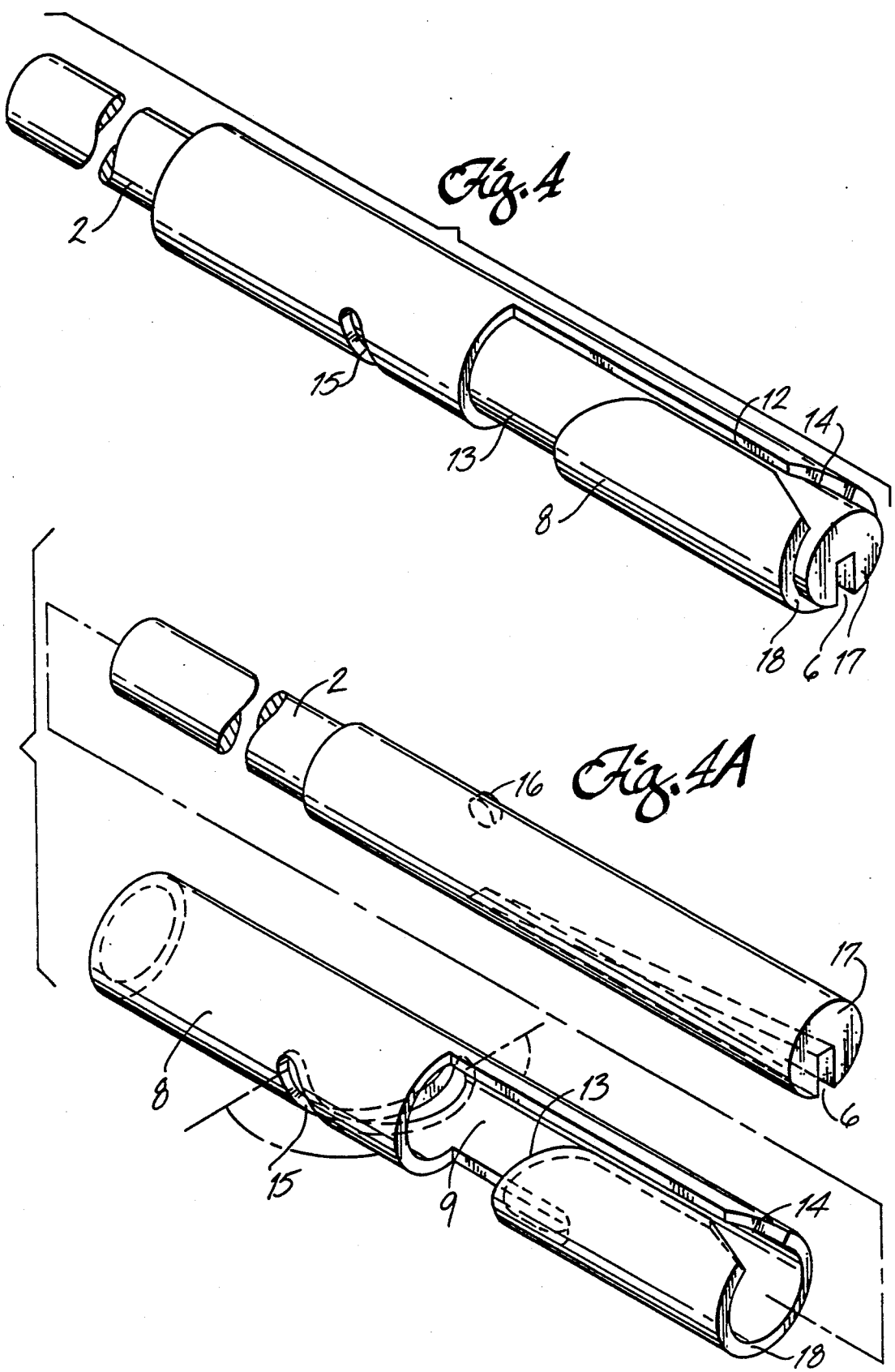

ENDOSCOPIC KNOT PUSHING INSTRUMENT

FIELD OF THE INVENTION

This invention relates to a surgical instrument for pushing a slip-knot formed extracorporeally through a trocar to a body cavity in the formation of a ligature during endoscopic surgery.

BACKGROUND OF THE INVENTION

In laparoscopic surgery, suturing and ligating requires the introduction of suture material into the abdominal cavity by passing the suture through a trocar. After introduction of the suture into the body cavity, the distal end of the suture material is then grasped with a grasper instrument to form either an endosuture (with a needle) or endoligature (without a needle). The grasper tool in one technique may be used to grasp the needle, snare the body structure, and then form a slip-knot intracorporeally; in another technique the free end of the suture material may be looped around a body structure such as a tube or vessel thereby forming a bight and the free end withdrawn through the trocar for the formation of an extracorporeal slip-knot. A push rod is then used in either technique to tighten the slip-knot by pushing the knot toward the body structure.

In the prior art, where the slip-knot is formed using a needle, one type of push rod utilized an axially extending lumen through which the strand of suture material above the slip-knot was inserted extracorporeally; the push rod was then pushed to tighten the knot. Where the slip-knot was formed extracorporeally without the needle, however, push rods generally utilized a longitudinally extending slot contained in the outer surface and located at the distal end of the rod; this permitted the strand of suture above the slip-knot to be advanced through the slot while the tip of the push rod remained in continuous engagement with the slip-knot as the knot was advanced into the body cavity through the trocar. In pushing a slip-knot formed extracorporeally through the trocar, however, the strand of suture contained in the slot above the slip-knot, during manipulation of the push rod, has a tendency, depending upon the orientation of the push rod, to slip from the groove; this requires the upper strand of suture material to be rethreaded by the surgeon into the slot in order to continue to advance and thereafter tighten the knot. If the strand slipped from the slot while the knot was in the trocar, it was usually necessary to withdraw the rod, reinsert the suture strand into the slot and then advance the rod through the trocar until engagement with the knot. This procedure was time consuming and unreliable and resulted in the escape of $CO_2$ gas from the body cavity. Thus, the method of the prior art for pushing a knot formed extracorporeally through a trocar into the operative cavity increased the operative risk because of the additional time required to thread the strand of the suture material into the slot and then re-engage contact with the slip-knot for advancement through the trocar.

SUMMARY OF THE INVENTION

There is, therefore, provided according to the present invention, an endoscopic surgical instrument for pushing a slip-knot formed extracorporeally through a trocar and against a body structure to form a ligature where the strand of suture material above the slip-knot is retained within a distal suture slot while the knot is being tightened or pushed.

The present invention is directed to an endoscopic knot pushing instrument of the type having an elongated cylindrical member which has an axially extending continuously open tapered groove contained in the distal surface of the member. The distal slot extends axially from the distal tip of the elongated member and extends at least in part towards the proximate end; the slot has a radially extending opening at the distal terminus of the elongated member which forms the maximum depth of the slot and permits the suture strand to advance axially through the slot; the slot tapers linearly from the distal end with diminishing depth as the slot extends proximately from the distal terminus. A locking sleeve having an axially extending cavity therethrough is carried by the elongated member and adapted for rotation relative to it. The locking sleeve is so dimensioned and proportioned to receive the distal end of the elongated member to permit rotation relative to the member and has an axially extending distal slit which communicates with the cavity. Rotation of the sleeve to a first position permits the slit to be aligned with the axially extending slot. Upon alignment of the slot and slit, the strand of suture material above the slip-knot formed extracorporeally may be inserted into the slot through the slit and upon rotation of the sleeve to a second position the suture strand will be locked in the slot by the sleeve thereby captively retaining the suture strand in the slot while at the same time permitting the strand to advance axially through the slot. In one embodiment of this invention, the distal tip portion of the elongated member containing the slot may be a sleeve member made of a plastic material insertable over the distal tip of an elongated rod and rigidly mounted thereby forming the elongated member. In another embodiment, the rod may be one piece and the distal slot formed in the distal portion of the rod to form the elongated member.

Thus, an instrument for pushing a knot formed extracorporeally through a trocar is provided where the strand of suture above the slip-knot may be locked into an axially extending slot for advancement therethrough while being captively retained by a locking sleeve. The distal tip of the elongated member may now be utilized as an engagement surface to bear against the slip-knot and the slip-knot pushed along the strand of suture through the trocar and into the operative region where it may be tightened against the body structure to form a ligature while the suture strand is captively retained within the slot.

BRIEF DESCRIPTION OF THE DRAWINGS

These and other features and advantages will become appreciated as the same become better understood with reference to the following specification, claims and drawings wherein:

FIG. 1 is a perspective view illustrating the distal portion of the endoscopic knot pushing instrument with the slot in an open position.

FIG. 1A is an exploded perspective view of FIG. 1.

FIG. 2 is a rear perspective view of FIG. 1 illustrating the distal slot in an open position.

FIG. 2A is an exploded perspective view of FIG. 2.

FIG. 3 is a perspective view of the distal portion of the knot pushing instrument illustrating the instrument in another position where the distal slot is closed by the locking sleeve.

FIG. 3A is an exploded perspective view of FIG. 3.
FIG. 4 is a rear perspective view of FIG. 3.
FIG. 4A is an exploded perspective view of FIG. 4.

DETAILED DESCRIPTION

The knot pusher instrument of this invention is shown in a first position in perspective in FIG. FIG. 2 depicts, in perspective, a view of the instrument in a direction opposite from that shown in FIG. 1. The technique for forming a ligature endoscopically requires that the suture material be introduced into the body cavity or operative region by passing the suture material through a trocar. The free end of the suture material in one technique is introduced into the body cavity with a needle attached; the needle is grasped after introduction to the body cavity by a grasper tool endoscopically to form a loop to snare tissue, tubes or vessels and a slip-knot formed extracorporeally. The free end of the suture material may also be advanced through the trocar without a needle to the operative region where the free end is grasped by a grasper tool and looped about a body structure and then withdrawn through the trocar and a knot formed extracorporeally. The techniques for forming a slip-knot extracorporeally or intracorporeally are not illustrated in the drawings and are well known in the prior art.

To push an extracorporeally formed slip-knot through the trocar and into the operative region where the knot is to be tightened about a body structure requires a knot pusher instrument. In the prior art, the knot pusher instrument engaged the strand of suture material above the knot with the tip of the instrument bearing against the knot during the pushing and tightening sequence. The typical knot pushing instrument in the prior art utilized a longitudinally extending groove located in the distal surface portion of the instrument; under certain orientations of the knot pusher within the trocar, the strand of suture could not be retained in the groove, would slip out, and necessitate the surgeon relocating the suture strand into the slot. This procedure was excessively time consuming if the suture strand became disengaged while the knot was being advanced through the trocar.

Referring now to FIGS. 1 and 2, the knot pusher instrument 1 is shown in a first position and consists of an elongated rod 2 having an axis of elongation 3 where the elongated rod may be made preferably of a stainless steel material. At the distal end 4 of elongated rod 2, the rod contains a tapered axially extending slot 5 which has an opening 6 in the distal tip or terminus of the rod that communicates with tapered axially extending slot 5. As can be seen in FIGS. 1A and 2A, the distal end 4 of elongated rod 2 has a diameter that is larger than the diameter of the rod 2. This results in a transition shoulder 7 which acts as a retainment barrier for the locking sleeve 8.

FIG. 1A is an exploded perspective view which illustrates the locking sleeve 8 in positional relationship to the distal end 4 of elongated rod 2. As can be seen in FIG. 1A, locking sleeve 8 has an axially extending cavity 9 which communicates with proximate opening 10 and distal opening 11 forming a continuous passageway through the locking sleeve for receiving the distal end 4 of elongated rod 2. Locking sleeve 8 has an axially extending open slit 12 which communicates with the cavity 9 and distal opening 11. As more clearly seen in FIG. 2A, locking sleeve 8 has an open region 13 which communicates with the cavity 9 and axially extending slit 12. To facilitate the threading of the strand of suture material (not shown) into tapered axially extending slot 5, the distal portion 14 of the slit 12 is flared. Thus, the strand of suture above the slip knot may be directed into tapered axially extending slot 5 by engagement with the flared portion 14 of slit 12.

Locking sleeve 8 is mounted to elongated rod 2 so as to permit both rotation and axial advancement of the sleeve when the sleeve is rotated relative to the rod. This is achieved by guide slot 15 which communicates with cavity 9 and extends in helix fashion forming an arcuate opening through the surface of locking sleeve 8. A cylindrical guide member 16 extends radially from the surface of distal portion 4 of the rod and projects into guide slot 15. Thus, upon rotation of locking sleeve 8 relative to the rod, the axial advance of the locking sleeve during rotation is predetermined. FIGS. 3 and 4 illustrate the knot pusher instrument in a second position where the locking sleeve 8, has been rotated 180 degrees from its first position. In the second position as shown in FIGS. 1 and 2, the sleeve 8 captively retains the upper strand portion of the suture material within tapered axially extending slot 5 which permits the strand to advance through the slot axially while retaining the strand within the slot. FIGS. 3(a) and 4(a) and exploded rear perspective views of FIGS. 3 and 4 respectively. It can be seen that FIG. 4 depicts a view of the instrument in perspective in a direction opposite to that of FIG. 3; in FIGS. 3 and 4(a), for example, the opening 6 in elongated rod 2 is shown at the lower right of FIGS. 4 and 4(a) with the open region 13 frontally displayed. In FIG. 3, on the other hand, the opening 6 (not shown) would be in the upper left of the figure with open region 13 rearwardly displayed. As can be seen in FIG. 4, the distal engagement surface 17 of elongated rod 2 extends beyond the distal boundary of the locking sleeve 8 which permits the continuous bearing of distal engagement surface 17 with the slip-knot formed in the suture material. When, therefore, the surgeon desires to push the slip-knot into the operative region through the trocar, the strand of suture above the slip-knot is placed within tapered axially extending slot 5 after the slit 12 is aligned with slot 5. The strand is captively retained within the slot by rotation of locking sleeve 8 to the second position. While the slip-knot is pushed through the trocar, the suture strand advances axially through slot 5 as the knot descends into the body cavity.

While I have shown and described an embodiment of the present knot pushing instrument, it is to be understood that it is subject to many modifications without departing from the spirit and scope of the claims as recited herein.

What is claimed is:

1. An instrument for pushing a knot through a trocar to the operative region during endoscopic surgery comprising:

a) an elongated member having a proximate and a distal end and having a longitudinal axis and a longitudinally extending surface containing a slot therein, said slot extending at least in part from said distal end in an axial direction toward said proximate end, and having an opening in said distal end, said elongated member having a lateral engagement surface coincident with and defining said distal end for bearing against said knot, and where said slot is of sufficient depth and so dimensioned and proportioned to permit a strand of suture to be retained within said slot during advancement of said strand of suture axially therethrough; and b) a locking sleeve having a proximate end and a distal end and an axially extending cavity therethrough for receiving said distal end of said elongated member, where said locking sleeve is carried by said elongated member and adapted for rotation relative thereto, said locking sleeve having an axially extending distal slit communicating with said cavity such that upon rotation of said locking sleeve to a first position said slit may be aligned with said slot to permit the insertion of said suture strand into said slot and upon sufficient rotation of said locking sleeve to a second position said slot may be sufficiently covered by said locking sleeve thereby retaining said suture strand within said slot during axial advancement of said strand through said slot, and (c) guide means associated with said elongated member and said locking sleeve for directionally guiding said locking sleeve from said first position to said second position and from said second position to said first position.

2. The instrument recited in claim 1 wherein said guide means comprises an arcuate slot in the surface of said locking sleeve communicating with said cavity and a guide member carried by said elongated member in fixed relationship therewith and projecting radially therefrom for extension into said arcuate slot.

3. The instrument recited in claim 2 wherein said arcuate slot is so disposed for sliding engagement with said guide member to permit axial advance of said sleeve upon rotation of said sleeve from said first position to said second position and from said second position to said first position.

4. The instrument recited in claim 1 wherein said slot has a linearly decreasing depth in an axial direction from said distal end of said elongated member toward said proximate end.

5. An improved instrument for pushing a knot through a trocar to the operative region during endoscopic surgery of the type having an elongated member having a proximate end and a distal end and having a longitudinal axis and a longitudinally extending surface containing a slot therein, said slot extending at least in part from said distal end of said elongated member in an axial direction toward said proximate end and having an opening in said distal end, where said slot is of sufficient depth and so dimensioned and proportioned to retain a strand of suture within said slot during advancement of said strand axially therethrough, the improvement comprising a locking sleeve carried by said elongated member and adapted for rotation relative thereto, said locking sleeve having an axially extending distal slit communicating with said cavity such that upon rotation of said locking sleeve to a first position said slit may be aligned with said slot to permit the insertion of said suture strand into said slot and upon sufficient rotation of said locking sleeve to a second position said slot may be sufficiently covered by said locking sleeve thereby retaining said suture strand within said slot during axial advancement of said strand through said slot, and guide means associated with said elongated member and said locking sleeve for directionally guiding said locking sleeve from said first position to said second position and from said second position to said first position.

6. The instrument recited in claim 5 wherein said guide means comprises an arcuate slot in the surface of said locking sleeve communicating with said cavity and a guide member carried by said elongated member in fixed relationship therewith and projecting radially therefrom for extension into said arcuate slot.

7. The instrument recited in claim 6 wherein said arcuate slot is so disposed for sliding engagement with said guide member to permit axial advance of said sleeve upon rotation of said sleeve from said first position to said second position and from said second position to said first position.

8. The instrument recited in claim 5 wherein said slot has a linearly decreasing depth in an axial direction from said distal end of said elongated member toward said proximate end.

9. An instrument for pushing a knot through a trocar to the operative region during endoscopic surgery comprising:

(a) an elongated member having a proximate end and a distal end and having a longitudinal axis and an open surface slot extending at least in part from said distal end in a direction toward said proximate end, where said elongated member has a radially extending opening at the distal end of said elongated member communicating with said slot and said slot is so dimensioned and proportioned to permit the advancement of a strand of suture axially therethrough and where said slot has a linearly decreasing depth in an axial direction from said distal end of said elongated member toward said proximate end; and (b) a locking sleeve having a proximate end and a distal end and an axially extending cavity therethrough for receiving said distal end of said elongated member, where said locking sleeve is carried by said elongated member and adapted for rotation relative thereto, said locking sleeve having an axially extending distal slit communicating with said cavity such that upon rotation of said locking sleeve to a first position said slit may be aligned with said slot to permit the insertion of said suture strand into said slot and upon sufficient rotation of said locking sleeve to a second position said slot may be sufficiently covered by said locking sleeve thereby retaining said suture strand within said slot during axial advancement of said strand through said slot; and (c) guide means associated with said elongated member and said locking sleeve for directionally guiding said locking sleeve from said first position to said second position and from said second position to said first position.

10. The instrument recited in claim 9 wherein said guide means comprises an arcuate slot in the surface of said locking sleeve communicating with said cavity and a guide member carried by said elongated member in fixed relationship therewith and projecting radially therefrom for extension into said arcuate slot.

11. The instrument recited in claim 10 wherein said arcuate slot is so disposed for sliding engagement with said guide member to permit axial advance of said sleeve upon rotation of said sleeve from said first position to said second position and from said second position to said first position.

12. An improved instrument for pushing a knot through a trocar to the operative region during endoscopic surgery of the type having an elongated member having a proximate and distal end and a longitudinal axis, said elongated member having an open surface slot extending at least in part from said distal end of said elongated member axially toward said proximate end of said elongated member, where said elongated member has a radially extending opening at said distal end of said elongated member communicating with said slot and said slot is so dimensioned and proportioned to permit the advancement of a strand of suture axially therethrough and where said slot has a linearly decreasing depth in an axial direction from said distal end of said elongated member toward said proximate end, the improvement comprising a locking sleeve carried by said elongated member and adapted for rotation relative thereto, said locking sleeve having an axially extending distal slit communicating with said cavity such that upon rotation of said locking sleeve to a first position said slit may be aligned with said slot to permit the insertion of said suture strand into said slot and upon sufficient rotation of said locking sleeve to a second position said slot may be sufficiently covered by said locking sleeve thereby retaining said suture strand within said slot during axial advancement of said strand through said slot, and guide means associated with said elongated member and said locking sleeve for directionally guiding said locking sleeve from said first position to said second position and from said second position to said first position.

13. The instrument recited in claim 12 wherein said guide means comprises an arcuate slot in the surface of said locking sleeve communicating with said cavity and a guide member carried by said elongated member in fixed relationship therewith and projecting radially therefrom for extension into said arcuate slot.

14. The instrument recited in claim 13 wherein said arcuate slot is so disposed for sliding engagement with said guide member to permit axial advance of said sleeve upon rotation of said sleeve from said first position to said second position and from said second position to said first position.

* * * * *